(12) United States Patent
Korth et al.

(10) Patent No.: US 8,138,365 B2
(45) Date of Patent: Mar. 20, 2012

(54) METHOD FOR PRODUCING ORGANOSILANES

(75) Inventors: Karsten Korth, Grenzach-Wyhlen (DE); Philipp Albert, Lörrach (DE); Susann Witzsche, Rheinfelden (DE); Ingo Kiefer, Schwörstadt-Dossenbach (DE); Jörg Kiefer, Schopfheim (DE); Stefan Lotter, Pulheim (DE); Jaroslaw Monkiewicz, Rheinfelden (DE); Jörg Schmidt, Bad Säckingen (DE)

(73) Assignee: Evonik Degussa GmbH, Essen (DE)

( * ) Notice: Subject to any disclaimer, the term of this patent is extended or adjusted under 35 U.S.C. 154(b) by 366 days.

(21) Appl. No.: 12/310,549

(22) PCT Filed: Jun. 11, 2007

(86) PCT No.: PCT/EP2007/055708

§ 371 (c)(1),
(2), (4) Date: Apr. 9, 2009

(87) PCT Pub. No.: WO2008/025580

PCT Pub. Date: Mar. 6, 2008

(65) Prior Publication Data

US 2010/0217026 A1 Aug. 26, 2010

(30) Foreign Application Priority Data

Sep. 1, 2006 (DE) .......................... 10 2006 041 356

(51) Int. Cl.
*C07F 7/00* (2006.01)
*C07F 7/04* (2006.01)

(52) U.S. Cl. ........................................ 556/466; 556/427

(58) Field of Classification Search .................... None
See application file for complete search history.

(56) References Cited

U.S. PATENT DOCUMENTS

| 4,629,775 | A | 12/1986 | Arai et al. |
| 4,654,368 | A | 3/1987 | Sakamoto et al. |
| 5,107,009 | A | 4/1992 | Rauleder et al. |
| 5,399,739 | A | * | 3/1995 | French et al. ................. 556/427 |
| 5,840,952 | A | 11/1998 | Kudo et al. |
| 5,859,275 | A | 1/1999 | Munzenberg et al. |
| 6,066,752 | A | 5/2000 | Takata et al. |
| 6,423,859 | B1 | 7/2002 | Alig et al. |
| 6,465,672 | B2 | 10/2002 | Michel et al. |
| 6,680,398 | B1 | 1/2004 | Boswell et al. |
| 6,740,767 | B1 | 5/2004 | Buesing et al. |
| 6,777,474 | B2 | 8/2004 | Yanagisawa |
| 6,995,280 | B2 | 2/2006 | Korth et al. |
| 7,288,667 | B2 | 10/2007 | Yanagisawa |
| 7,309,797 | B2 | 12/2007 | Yanagisawa |
| 7,368,588 | B2 | 5/2008 | Yanagisawa |
| 7,371,881 | B2 | 5/2008 | Frings et al. |
| 7,384,997 | B2 | 6/2008 | Hasse et al. |
| 7,501,534 | B2 | 3/2009 | Korth et al. |
| 7,777,063 | B2 | 8/2010 | Korth et al. |
| 2001/0037034 | A1 | 11/2001 | Michel et al. |
| 2003/0176719 | A1 | 9/2003 | Yanagisawa et al. |
| 2005/0124821 | A1 | 6/2005 | Korth et al. |
| 2006/0052621 | A1 | 3/2006 | Korth et al. |
| 2006/0094892 | A1 | 5/2006 | Yanagisawa et al. |
| 2006/0161015 | A1 | 7/2006 | Klockmann et al. |

FOREIGN PATENT DOCUMENTS

| DE | 196 51 849 A1 | 6/1998 |
| DE | 103 51 735 B3 | 12/2004 |
| DE | 10 2005 052 233 A1 | 9/2006 |
| EP | 0 471 164 A1 | 2/1992 |
| EP | 0 848 006 A2 | 6/1998 |
| EP | 0 949 263 A2 | 10/1999 |
| EP | 1130023 | * | 2/2001 |
| EP | 1 130 023 A2 | 9/2001 |
| EP | 1 172 367 A2 | 1/2002 |
| EP | 1172367 | * | 1/2002 |
| GB | 1 102 251 | 2/1968 |
| WO | 03/002573 | * | 1/2003 |
| WO | 03/002577 | * | 1/2003 |
| WO | WO 03/002573 A2 | 1/2003 |
| WO | WO 03/002577 A1 | 1/2003 |
| WO | WO 2004/043969 A1 | 5/2004 |

OTHER PUBLICATIONS

International Search Report for PCT/EP2007/055708 filed Jun. 11, 2007.
Written Opinion of the International Searching Authority for PCT/EP2007/055708 filed Jun. 11, 2007.
English translation of the Written Opinion of the International Searching Authority for PCT/EP2007/055708 filed Jun. 11, 2007.
English Translation of International Preliminary Report on Patentability for PCT/EP2007/055708 issued Mar. 17, 2009.

* cited by examiner

*Primary Examiner* — Karl J Puttlitz
(74) *Attorney, Agent, or Firm* — Law Office of: Michael A. Sanzo, LLC

(57) ABSTRACT

The invention relates to a method for producing organosilanes of general formula I,

[R(R)(R'O)Si—R''—]$_2$S$_m$   I by reaction of (halo-organo)alkoxysilanes of formula II,

[R(R)(R'O)Si—R''-Hal   II with a sulfuring reagent, selected from alkaline hydrogensulfide, alkaline sulfide Me$_2$S, alkaline polysulfide Me$_2$S$_g$ and any combination thereof and optionally additionally with sulfur and/or with H$_2$S in a solvent, the alkaline hydroxy content of all materials used being <0.44 wt. %.

20 Claims, No Drawings

METHOD FOR PRODUCING ORGANOSILANES

CROSS REFERENCE TO RELATED APPLICATIONS

The present application is US national stage of international application PCT/EP2007/055708, which had an international filing date of Jun. 11, 2007, and which was published in German under PCT Article 21(2) on Mar. 6, 2008. The international application claims priority to German application DE 10 2006 041 356.3, filed on Sept. 1, 2006. To the extent permitted by law, all prior applications are hereby incorporated by reference in their entirety.

The invention relates to a process for preparing organosilanes.

EP 1130023 discloses the preparation of organosilylalkylpolysulfanes of the general formula $$(R^1R^2R^3Si-R^4-)_2S_q$$

from the organosilylalkyl halide. The reaction is carried out by initially charging elemental sulfur and the organylalkyl halide in a polar organic solvent and adding anhydrous or virtually anhydrous ionic sulfide to this suspension. Owing to the hydrolysis susceptibility of the Si-alkoxy bonds of the organosilylalkyl halide, the ionic sulfides must be anhydrous or virtually anhydrous.

In addition, WO2003002577 A1 discloses the synthesis of organosilylalkylpolysulfanes in the presence of alkali metal hydroxides and the thermal treatment thereof (WO2004043969). In these known processes, larger amounts of NaOH can be used in the reaction mixture and contacted with the alkoxysilanes present therein.

DE 10 2005 052 233.5 discloses the synthesis of sulfur-containing alkoxysilanes using hydrous sulfurizing reagents in alcohol. In the case of use of different, commercially available raw materials, large differences in the monomer content of the resulting polysulfidic alkoxysilanes are found in tests on the production scale. It is thus impossible to achieve a reliable, homogeneous product quality on the industrial scale.

Disadvantages of the known processes are the use of anhydrous or virtually anhydrous starting materials and, in the case of hydrous starting materials, the significant variations in the product quality, especially the monomer content.

It is an object of the present invention to provide a process for preparing sulfur-containing organosilanes, which enables good crude product yields of >90% of theory and high monomer contents of >90% by weight with simultaneous use of hydrous sulfurizing reagents.

The invention provides a process for preparing organosilanes of the general formula I $$[R(R)(R'O)Si-R''-]_2S_m \qquad I$$

where

R is the same or different and is a $C_1$-$C_8$-alkyl, preferably $CH_3$ or $CH_2CH_3$, $C_1$-$C_8$-alkenyl, $C_1$-$C_8$-aryl, $C_1$-$C_8$-aralkyl group, or an OR' group, R' is the same or different and is a $C_1$-$C_{22}$, preferably $C_1$-$C_4$ or $C_{12}$-$C_{18}$, more preferably $CH_2CH_3$, branched or unbranched monovalent alkyl or alkenyl group, an aryl group, an aralkyl group, a hydrogen (—H), an alkyl ether group O—$(CR^{III}_2)$—O-Alk or O—$(CR^{III}_2)_y$—O-Alk or an alkyl polyether group O—$(CR^{III}_2O)_y$-Alk or O—$(CR^{III}_2—CR^{III}_2—O)_y$-Alk, where y=2-20, preferably 2-10, more preferably 3-8, exceptionally preferably 3-6, $R^{III}$ is independently H or an alkyl group, preferably $CH_3$ group, and Alk is a branched or unbranched, saturated or unsaturated, aliphatic, aromatic or mixed aliphatic/aromatic monovalent $C_1$-$C_{22}$, preferably $C_2$-$C_{20}$, more preferably $C_6$-$C_{18}$, most preferably $C_{10}$-$C_{18}$, hydrocarbon group, R" is a branched or unbranched, saturated or unsaturated, aliphatic, aromatic or mixed aliphatic/aromatic divalent $C_1$-$C_{30}$, preferably $C_1$-$C_{20}$, more preferably $C_1$-$C_{10}$, most preferably $C_1$-$C_7$, hydrocarbon group which is optionally substituted by F, Cl, Br, I, HS, $NH_2$ or NHR', m is a mean sulfur chain length of from 1.5 to 4.5, by reacting (haloorganyl)alkoxysilane of the formula II

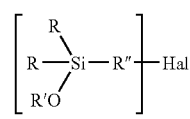

where

R, R' and R" are each as defined above and Hal is chlorine, bromine, fluorine or iodine with a sulfurizing reagent selected from the group of alkali metal hydrogensulfide, metal sulfide $Me_2S$, metal polysulfide $Me_2S_g$ and any desired combinations thereof, where Me=alkali metal, $NH_4$ or (alkaline earth metal)$_{1/2}$, and g=1.5-8.0, and optionally additionally with sulfur and/or with $H_2S$ in a solvent, which is characterized in that the alkali metal hydroxide content of all feedstocks is <0.44% by weight, preferably <0.35% by weight, more preferably <0.1% by weight, most preferably less than 0.05% by weight.

The alkali metal hydroxide content of all feedstocks is the sum of the alkali metal hydroxide contents of all substances which are added before, during or at the end of the reaction, neglecting the alkali metal hydroxide content of the (haloorganyl)alkoxysilanes of the general formula II and of the solvent.

The alkali metal hydroxide content of all feedstocks may be 0% by weight.

The alkali metal hydroxides may be LiOH, NaOH and KOH.

The alkali metal hydroxide content of all feedstocks may be 0.0001-0.44% by weight, preferably 0.0001-0.25% by weight, more preferably 0.0001-0.1% by weight, most preferably 0.001-0.015% by weight.

The lithium hydroxide content of all feedstocks may be 0.0001-0.44% by weight, preferably 0.0001-0.25% by weight, more preferably 0.0001-0.1% by weight, most preferably 0.001-0.015% by weight.

The sodium hydroxide content of all feedstocks may be 0.0001-0.44% by weight, preferably 0.0001-0.25% by weight, more preferably 0.0001-0.1% by weight, most preferably 0.001-0.015% by weight.

The potassium hydroxide content of all feedstocks may be 0.0001-0.45% by weight, preferably 0.0001-0.25% by weight, more preferably 0.0001-0.1% by weight, most preferably 0.001-0.015% by weight.

R" may be —$CH_2$—, —$CH_2CH_2$—, —$CH_2CH_2CH_2$—, —$CH_2CH_2CH_2CH_2$—, —$CH(CH_3)$—, —$CH_2CH(CH_3)$—, —$CH(CH_3)CH_2$—, —$C(CH_3)_2$—, —$CH(C_2H_5)$—, —$CH_2CH_2CH(CH_3)$—, —$CH_2CH(CH_3)CH_2$— or

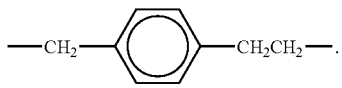

In the process according to the invention for preparing organosilanes, it is possible for compounds of the general formula I or else mixtures of compounds of the general formula I to form.

The mixtures of organosilanes of the general formula I may have a mean sulfur chain length determinable by HPLC+GC of m=1.5-4.5, where the individual organosilanes may have sulfur chains with S1 to S12.

The mean sulfur chain length m, determined by GC and HPLC or NMR, may be from 1.5 to 4.5, preferably from 2 to 2.8 or from 3.0 to 4, more preferably from 2 to 2.5 or from 3.4 to 3.8.

Compounds of the general formula I which form mixtures having a mean sulfur chain length of m=1.5-4.5 are described, for example, in DE 10 2005 052 233.5 and may preferably be
[(MeO)$_3$Si (CH$_2$)$_3$]$_2$S, [(MeO)$_3$Si (CH$_2$)$_3$]$_2$S$_2$,
[(MeO)$_3$Si (CH$_2$)$_3$]$_2$S$_3$, [(MeO)$_3$Si (CH$_2$)$_3$]$_2$S$_4$,
[(MeO)$_3$Si (CH$_2$)$_3$]$_2$S$_5$, [(MeO)$_3$Si (CH$_2$)$_3$]$_2$S$_6$,
[(MeO)$_3$Si (CH$_2$)$_3$]$_2$S$_7$, [(MeO)$_3$Si (CH$_2$)$_3$]$_2$S$_8$,
[(MeO)$_3$Si (CH$_2$)$_3$]$_2$S$_9$, [(MeO)$_3$Si (CH$_2$)$_3$]$_2$S$_{10}$,
[(EtO)$_3$Si (CH$_2$)$_3$]$_2$S, [(EtO)$_3$Si (CH$_2$)$_3$]$_2$S$_2$,
[(EtO)$_3$Si (CH$_2$)$_3$]$_2$S$_3$, [(EtO)$_3$Si (CH$_2$)$_3$]$_2$S$_4$,
[(EtO)$_3$Si (CH$_2$)$_3$]$_2$S$_5$, [(EtO)$_3$Si (CH$_2$)$_3$]$_2$S$_6$,
[(EtO)$_3$Si (CH$_2$)$_3$]$_2$S$_7$, [(EtO)$_3$Si (CH$_2$)$_3$]$_2$S$_8$,
[(EtO)$_3$Si (CH$_2$)$_3$]$_2$S$_9$, [(EtO)$_3$Si (CH$_2$)$_3$]$_2$S$_{10}$,
[(C$_3$H$_7$O)$_3$Si (CH$_2$)$_3$]$_2$S, [(C$_3$H$_7$O)$_3$Si (CH$_2$)$_3$]$_2$S$_2$,
[(C$_3$H$_7$O)$_3$Si (CH$_2$)$_3$]$_2$S$_3$, [(C$_3$H$_7$O)$_3$Si (CH$_2$)$_3$]$_2$S$_4$,
[(C$_3$H$_7$O)$_3$Si (CH$_2$)$_3$]$_2$S$_5$, [(C$_3$H$_7$O)$_3$Si (CH$_2$)$_3$]$_2$S$_6$,
[(C$_3$H$_7$O)$_3$Si (CH$_2$)$_3$]$_2$S$_7$, [(C$_3$H$_7$O)$_3$Si (CH$_2$)$_3$]$_2$S$_8$,
[(C$_3$H$_7$O)$_3$Si (CH$_2$)$_3$]$_2$S$_9$ or [(C$_3$H$_7$O)$_3$Si (CH$_2$)$_3$]$_2$S$_{10}$.

The alkyl polyether group in formula I and II may contain ethylene oxide (CH$_2$—CH$_2$—O) and propylene oxide units, for example (CH(CH$_3$)—CH$_2$—O) or (CH$_2$—CH(CH$_3$)—O).

The alkyl polyether group O—(CR$^{III}$$_2$O)$_y$-Alk or O—(CR$^{III}$$_2$—CR$^{III}$$_2$O)$_y$-Alk may correspond to those alkyl polyether groups described in DE 10 2005 052 233.5.

The (haloorganyl)alkoxysilanes of the formula II used may be the (haloorganyl)alkoxysilanes described in DE 10 2005 052 233.5.

The (haloorganyl)alkoxysilanes of the formula II used may preferably be
3-chlorobutyl(triethoxysilane),
3-chlorobutyl(trimethoxysilane),
3-chlorobutyl(diethoxymethoxysilane),
3-chloroisobutyl(triethoxysilane),
3-chloroisobutyl(trimethoxysilane),
3-chloroisobutyl(diethoxymethoxysilane),
3-chloropropyl(triethoxysilane),
3-chloropropyl(trimethoxysilane),
3-chloropropyl(diethoxymethoxysilane),
2-chloroethyl(triethoxysilane),
2-chloroethyl(trimethoxysilane),
2-chloroethyl(diethoxymethoxysilane),
1-chloromethyl(triethoxysilane),
1-chloromethyl(trimethoxysilane),
1-chloromethyldiethoxymethoxysilane),
3-chlorobutyl(diethoxymethylsilane),
3-chlorobutyl(dimethoxymethylsilane),
3-chloroisobutyl(dimethoxymethylsilane),
3-chloroisobutyl(diethoxymethylsilane),
3-chloropropyl(diethoxymethylsilane),
3-chloropropyl(dimethoxymethylsilane),
2-chloroethyl(diethoxymethylsilane),
2-chloroethyl(dimethoxymethylsilane),
1-chloromethyl(diethoxymethylsilane),
1-chloromethyl(dimethoxymethylsilane),
3-chlorobutyl(ethoxydimethylsilane),
3-chlorobutyl(methoxydimethylsilane),
3-chloroisobutyl(methoxydimethylsilane),
3-chloroisobutyl(ethoxydimethylsilane),
3-chloropropyl(ethoxydimethylsilane),
3-chloropropyl(methoxydimethylsilane),
2-chloroethyl(ethoxydimethylsilane),
2-chloroethyl(methoxydimethylsilane),
1-chloromethyl(ethoxydimethylsilane) and
1-chloromethyl(methoxydimethylsilane).

The (haloorganyl)alkoxysilane may be a (haloorganyl)alkoxysilane of the formula II or a mixture of (haloorganyl)alkoxysilanes of the formula II.

The molar amount of the (haloorganyl)alkoxysilane used may exceed the sum of the molar amounts of sulfurizing reagents, for example Me$_2$S, MeSH or/and Me$_2$S$_g$, by from 0.05 mol % to 50 mol %, preferably by from 0.5 to 20 mol %, more preferably by from 0.5 to 10 mol %, most preferably by from 1 to 6 mol %.

The sulfur used may have an average particle size of >100 µm, preferably >200 µm, more preferably >500 µm, most preferably >2000 µm, when a virtually dust-free material is required.

The sulfur used may have an average particle size of <100 µm and >1 µm, preferably of <80 µm and >1 µm, more preferably of <65 µm and >5 µm, most preferably of <50 µm and >5 µm, when a material with a high specific surface area is required.

The sulfur used may have an average particle size of <500 µm, preferably <250 µm, more preferably <100 µm, most preferably <80 µm, when a material with a high, specific surface area is required.

The particle size distribution of the sulfur is determined by laser diffraction analysis without ultrasound treatment with a Coulter LS 100 with a dry powder module (from Beckman-Coulter) according to the commonly known rules and operation instructions. For 60 sec, a continuous stream of original, untreated particles of the sample to be analyzed is conducted through a laser beam in an air jet. The beam passes through the particle stream and the different particle sizes are detected and evaluated statistically. The measurable particle size is at least 0.4 µm and at most 900 µm.

The sulfur used may have an average particle size after screening of <20000 µm and >1 µm, preferably of <15 000 µm and >100 µm, more preferably of <12 000 µm and >500 µm, most preferably of <10 000 µm and >2000 µm, when a low-dust material with a high bulk density is required.

The particle fractions of the sulfur after screening are determined as follows:

The particle fractions of preshaped, granulated, microgranulated or microbeaded sulfur are determined by screening. To this end, a particular amount of sulfur particles is separated with a stack of screens of different, standardized mesh size.

By weighing, the proportion of the individual fractions is determined. The equipment used for this purpose: mechanical screening machine (Ro-tap); precision balance: accuracy ±0.01 g (from Mettler)

US. standard screens No. 120, height 25 mm, Ø: 200 mm; mesh sizes for example: 300 μm (50 mesh); 150 μm (100 mesh); 75 μm (200 mesh).

The screens and a collecting vessel are assembled in the intended sequence, i.e. with opening width decreasing from the top downward. 100 g of the sample to be studied are weighed out, using an appropriate shovel. A preliminary selection of the material by pouring or transferring the shaped sulfur particles out of the stock vessel should be avoided. After the weighed sulfur particles have been transferred onto the uppermost screen, a lid is placed on and the stack is inserted into the screening machine such that a clearance of approx. 1.5 mm remains and the screens can thus rotate freely.

The screens are secured in the machine and then shaken for 5 min—with the shaker or vibrator system in operation. Thereafter, the screens are taken apart successively and the amount of sulfur particles present in each is weighed accurately to 0.1 g. A double determination of each sample is carried out. In each case, the mean of the amounts of sulfur particles found in the individual screens and in the collecting vessel is reported in %.

The sulfurizing reagent and any sulfur and/or $H_2S$ may be alkali metal hydrogensulfide, $Me_2S$, $Me_2S_g$, alkali metal hydrogensulfide+sulfur, $Me_2S$+sulfur, $Me_2S_g$+sulfur, alkali metal hydrogensulfide+$Me_2S_g$+$Me_2S$, $Me_2S_g$+$Me_2S$, alkali metal hydrogensulfide+$Me_2S$+sulfur, alkali metal hydrogensulfide+$Me_2S_g$+sulfur, $Me_2S$+$Me_2S_g$+sulfur, alkali metal hydrogensulfide+$Me_2S_g$+$Me_2S$+sulfur, $H_2S$+$Me_2S_g$+$Me_2S$+sulfur, $H_2S$+alkali metal hydrogensulfide+$Me_2S_g$+$Me_2S$+sulfur, $H_2S$+alkali metal hydrogensulfide+$Me_2S_g$+$Me_2S$, $H_2S$+alkali metal hydrogensulfide+$Me_2S$, $H_2S$+alkali metal hydrogensulfide+$Me_2S_g$, $H_2S$+$Me_2S$+sulfur, $H_2S$+$Me_2S_g$+sulfur, $H_2S$+$Me_2S_g$+$Me_2S$, $H_2S$+$Me_2S_g$ and $H_2S$+$Me_2S$.

The alkali metal hydrogensulfide used may be lithium hydrogensulfide (LiSH), sodium hydrogensulfide (NaSH), potassium hydrogensulfide (KSH) and cesium hydrogensulfide (CsSH).

The alkali metal sulfide $Me_2S$ or alkali metal polysulfide $Me_2S_g$ used may be $Li_2S$, $Na_2S$, $K_2S$, $Na_2S_2$, $Na_2S_3$, $Na_2S_4$, $Na_2S_5$, $Na_2S_6$, $K_2S_2$, $K_2S_3$, $K_2S_4$, $K_2S_5$, $K_2S_6$ or mixtures thereof.

The hydrous sulfurizing reagents used may be added to the reaction as solids or in solution.

The solid hydrous sulfurizing reagents may contain less than 60% by weight, preferably less than 50% by weight, more preferably less than 40% by weight, most preferably less than 35% by weight, of water.

Preferably, the solid, hydrous sulfurizing reagents of the $Me_2S_g$ form may contain less than 60% by weight, preferably less than 50% by weight, more preferably less than 40% by weight, most preferably less than 35% by weight, of water.

The hydrous sulfurizing reagents may contain between 10 and 60% by weight, preferably between 10 and 50% by weight, more preferably between 15 and 35% by weight, of water.

The hydrous sulfurizing reagents may, as well as water, contain further secondary constituents to an extent of less than 30% by weight, preferably less than 20% by weight, more preferably less than 10% by weight, most preferably less than 5% by weight.

The solid hydrous alkali metal hydrogensulfides may contain more than 50% by weight, preferably more than 60% by weight, more preferably more than 65% by weight, most preferably more than 70% by weight, of alkali metal hydrogensulfide.

Further secondary constituents of hydrous sulfurizing reagents may, as well as water, independently be alkali metal carbonates, alkali metal hydrogencarbonates, alkali metal sulfates, alkali metal hydrogensulfates, alkali metal thiosulfates and/or alkali metal hydrogenthiosulfates.

The water content of the sulfurizing reagents is determined as follows: for the water content determination, glass beads are moistened slightly, covered with phosphorus pentoxide and then filled into a U-tube. Approx. 3 g of the sample are weighed into a 50 ml flask, baked out at 320° C. under a Sicapent-dried nitrogen stream (30 ml/min) for 2 hours and then left to stand under a nitrogen stream for another 30 min. The moist carrier gas is passed via a pipe connection from the flask into the U-tube. Possible condensation between the flask and U-tube is driven out during the baking-out phase with the aid of a hot-air gun. The U-tube is weighed again and the amount of water released from the sulfurizing reagents is determined gravimetrically.

Solutions of sulfurizing reagents may contain more than 5% by weight, preferably more than 10% by weight, more preferably more than 15% by weight, most preferably more than 20% by weight, of sulfurizing reagents.

Solutions of sulfurizing reagents may be sulfurizing reagents dissolved in water.

The solvents used for the process may be hydrous solvents.

The hydrous solvents may be alcohols.

The alcohols used may be mixtures of alcohols.

The alcohols used may be primary, secondary or tertiary alcohols having from 1 to 24, preferably from 1 to 6 and more preferably from 1 to 4, carbon atoms.

The alcohols used may be alkyl ethers of the formula HO—$(CR^{IV}_2)$—O-Alk' or HO—$(CR^{IV}_2)_{y'}$—O-Alk', or alkyl polyethers of the formula HO— $(CR^{IV}_2O)_{y'}$-Alk' or HO— $(CR^{IV}_2$—$CR^{IV}_2$—$O)_{y'}$-Alk', where y'=2-20, preferably 2-10, more preferably 3-6, $R^{IV}$ is independently H or an alkyl group, preferably a $CH_3$ group, and Alk' is a branched or unbranched, saturated or unsaturated, aliphatic, aromatic or mixed aliphatic/aromatic monovalent $C_1$-$C_{22}$, preferably $C_2$-$C_{20}$, more preferably $C_6$-$C_{18}$ and most preferably $C_{10}$-$C_{18}$ hydrocarbon group.

The primary, secondary or tertiary alcohols used may be methanol, ethanol, n-propanol, i-propanol, i-butanol, n-butanol, n-hexanol, i-hexanol, cyclohexanol, octanol, dodecanol, tetradecanol, hexadecanol or octadecanol. The alkyl polyethers used may be HO— $(CH_2$—$CH_2$—$O)_a$—$C_bH_{2b+1}$, where a is from 2 to 20, preferably 2-10, more preferably 2-8, most preferably 3-6, and b=1-22, preferably 2-20, more preferably 6-18, most preferably 10-18.

Primary alcohols may be
HO—$(CH_2$—$CH_2$—$O)_2$—$C_6H_{13}$, HO—$(CH_2$—$CH_2$—$O)_3$—$C_6H_{13}$, HO—$(CH_2$—$CH_2$—$O)_4$—$C_6H_{13}$, HO—$(CH_2$—$CH_2$—$O)_5$—$C_6H_{13}$, HO—$(CH_2$—$CH_2$—$O)_6$—$C_6H_{13}$, HO—$(CH_2$—$CH_2$—$O)_7$—$C_6H_{13}$, HO—$(CH_2$—$CH_2$—$O)_8$—$C_6H_{13}$, HO—$(CH_2$—$CH_2$—$O)_9$—$C_6H_{13}$,
HO—$(CH_2$—$CH_2$—$O)_2$—$C_{10}H_{21}$, HO—$(CH_2$—$CH_2$—$O)_3$—$C_{10}H_{21}$, HO—$(CH_2$—$CH_2$—$O)_4$—$C_{10}H_{21}$, HO—$(CH_2$—$CH_2$—$O)_5$—$C_{10}H_{21}$, HO—$(CH_2$—$CH_2$—$O)_6$—$C_{10}H_{21}$, HO—$(CH_2$—$CH_2$—$O)_7$—$C_{10}H_{21}$, HO—$(CH_2$—$CH_2$—$O)_8$—$C_{10}H_{21}$, HO—$(CH_2$—$CH_2$—$O)_9$—$C_{10}H_{21}$,
HO—$(CH_2$—$CH_2$—$O)_2$—$C_{13}H_{27}$, HO—$(CH_2$—$CH_2$—$O)_3$—$C_{13}H_{27}$, HO—$(CH_2$—$CH_2$—$O)_4$—$C_{13}H_{27}$, HO—$(CH_2$—$CH_2$—$O)_5$—$C_{13}H_{27}$, HO—$(CH_2$—$CH_2$—$O)_6$—$C_{13}H_{27}$, HO—$(CH_2$—$CH_2$—$O)_7$—$C_{13}H_{27}$, HO—$(CH_2$—$CH_2$—$O)_8$—$C_{13}H_{27}$, HO—$(CH_2$—$CH_2$—$O)_9$—$C_{13}H_{27}$,
HO—$(CH_2$—$CH_2$—$O)_2$—$C_{15}H_{31}$, HO—$(CH_2$—$CH_2$—$O)_3$—$C_{15}H_{31}$, HO—$(CH_2$—$CH_2$—$O)_4$—$C_{15}H_{31}$, HO—$(CH_2$—$CH_2$—$O)_5$—$C_{15}H_{31}$, HO—$(CH_2$—$CH_2$—$O)_6$—

$C_{15}H_{31}$, HO—$(CH_2$—$CH_2$—O)$_7$—$C_{15}H_{31}$, HO—$(CH_2$—$CH_2$—O)$_8$—$C_{15}H_{31}$ or HO—$(CH_2$—$CH_2$—O)$_9$—$C_{15}H_{31}$.

The amount of solvent added may be at least 1% by weight, preferably from 10 to 800% by weight, more preferably from 10 to 150% by weight, even more preferably from 20 to 100% by weight, exceptionally preferably from 20 to 80% by weight, of the silane components used.

The amount of hydrous solvent added may be at least 1% by weight, preferably from 10 to 800% by weight, more preferably from 10 to 150% by weight, even more preferably from 20 to 100% by weight, exceptionally preferably from 20 to 100% by weight, of the silane components used.

The solvent used may contain more than 7.5% by weight, preferably more than 9% by weight, more preferably more than 14% by weight, especially preferably more than 19% by weight, of water.

The solvent may contain between 7.5 and 75% by weight, preferably between 7.5 and 49% by weight, more preferably between 7.5 and 30% by weight, especially preferably between 9 and 29% by weight, most preferably between 14 and 24% by weight, of water.

Additives can be added before, during or after the reaction.

Additives may be the additives named in DE 10 2005 052 233.5, excluding alkali metal hydroxides.

Additives may be nonalcoholic solvents.

Before, during or after the reaction, it is possible to add to the reaction mixture additives selected from the group of $H_2S$, $CO_2$ or a compound which is capable of reversibly or irreversibly releasing a proton to alkali metal hydrogensulfides in the pH range between 5 and 8.

Before, during or after the reaction, it is possible to add to the reaction mixture additives selected from the group of $H_2S$, $CO_2$ or a compound which is capable of reversibly or irreversibly releasing a proton to alkali metal sulfides in the pH range between 5 and 8.

Compounds which are capable of releasing a proton reversibly or irreversibly to alkali metal hydrogensulfides or alkali metal sulfides in the pH range between 5 and 8 may, for example, be organic or inorganic acids.

Organic acids and inorganic acids are described, for example, in DE 10 2005 052 233.5.

Organic acids may be compounds of the following base structures: alkyl-COOH, aryl-COOH, aralkyl-COOH, alkyl-S(O)$_2$OH, HOOC-alkylene-COOH, HOOC-aryl-COOH or HOOC-aralkyl-COOH.

Inorganic acids may, for example, be compounds of the composition HCl, $H_2SO_4$, $H_3PO_4$, (alkali metal ion)$H_2PO_4$, (alkali metal ion)$_2HPO_4$, $H_2CO_3$, (alkali metal ion) $HCO_3$, or (alkali metal ion)$HSO_4$.

At the start of the reaction and/or during the reaction and/or at the end of the reaction, it is possible to add polar, protic, aprotic, basic or acidic additives to the reaction mixture.

Acidic or basic additives which are added to the reaction mixture before, during or at the end of the process may have the structure (alkali metal ion)$H_2PO_4$, (alkali metal ion)$_2$$HPO_4$, (alkali metal ion)$_3PO_4$, (alkali metal ion)$HCO_3$, (alkali metal ion)$_2CO_3$, (alkali metal ion)$_2SO_4$ or (alkali metal ion)$HSO_4$. Compounds of the structure (alkali metal ion)$H_2PO_4$ may preferably be $KH_2PO_4$ and $NaH_2PO_4$. Compounds of the structure (alkali metal ion)$_2HPO_4$ may preferably be $K_2HPO_4$ and $Na_2HPO_4$. Compounds of the structure (alkali metal ion)$HCO_3$ may preferably be $KHCO_3$ and $NaHCO_3$. Compounds of the structure (alkali metal ion)$_2CO_3$ may preferably be $K_2CO_3$, $Li_2CO_3$ and $Na_2CO_3$. Compounds of the structure (alkali metal ion)$HSO_4$ may preferably be $KHSO_4$ and $NaHSO_4$.

Acidic or basic additives which are added to the reaction mixture before, during or at the end of the process may have an average particle size of >100 µm, preferably >200 µm, more preferably >500 µm, most preferably >2000 µm, when a virtually dust-free material is required.

Acidic or basic additives which are added to the reaction mixture before, during or at the end of the process may have an average particle size of <100 µm and >1 µm, preferably of <80 µm and >1 µm, more preferably of <65 µm and >5 µm, most preferably of <50 µm and >5 µm, when a material with a high specific surface area is required.

Acidic or basic additives which are added to the reaction mixture before, during or at the end of the process may have an average particle size of <500 µm, preferably <250 µm, more preferably <100 µm, most preferably <80 µm, when a material with a high specific surface area is required.

The particle size distribution of the samples of the solid acidic or basic additives is determined by laser diffraction analysis without ultrasound treatment with a Coulter LS 100 with a dry powder module (from Beckman-Coulter) according to the commonly known rules and operation instructions. For 60 sec., a continuous stream of original, untreated particles of the sample to be analyzed is conducted through a laser beam in an air stream. The beam passes through the particle stream and the different particle sizes are detected and evaluated statistically. The measurable particle size is a minimum of 0.4 µm and a maximum of 900 µm.

The (haloorganyl)alkoxysilane, additives, sulfurizing reagent and solvent may be mixed with one another in different sequences, ways, temperatures and durations familiar to the person skilled in the art.

Possible mixing sequences are described in DE 10 2005 052 233.5.

The sulfurizing reagents required for the reaction may be formed from sulfur-containing compounds before or during the reaction.

The sulfur-containing compounds may react under the reaction conditions, through protonation, completely or incompletely, reversibly or irreversibly, to give alkali metal hydrogensulfides or $H_2S$.

The sulfur-containing compounds may react under the reaction conditions, by deprotonation, completely or incompletely, reversibly or irreversibly, to give alkali metal sulfides or alkali metal hydrogensulfides.

The sulfur compounds from which alkali metal hydrogensulfides are formed before or during the reaction can be protonated by $H_2S$ and/or organic and/or inorganic acids.

The sulfur compounds from which alkali metal sulfides can be formed before or during the reaction can be deprotonated by organic and/or inorganic bases.

The deprotonation of $H_2S$, which can form alkali metal hydrogensulfides before or during the reaction, can be effected by organic and/or inorganic bases.

The reaction can be effected at temperatures between 0 and 150° C., preferably between 40 and 100° C., more preferably between 50 and 80° C.

During the workup of the crude products, the hydrous solvents can be removed under reduced pressure and at elevated temperature. It is possible to add and use water-entraining substances (azeotroping agents) known to those skilled in the art in order to remove, as well as the solvent, also water under reduced pressure at elevated temperature. The water present in the crude product can be removed from the crude product or the end product under reduced pressure at elevated temperature. For the removal of solvents, azeotroping agents and water, assistants and apparatus known to those skilled in the art can be used.

Preference may be given to using vertical tube evaporators, horizontal tube evaporators, inclined tube evaporators, falling-film evaporators, plate evaporators, blast pipe evaporators, rotor evaporators, centrifugal evaporators, screw evaporators, thin-layer evaporators and thin-film strippers.

The reaction can be effected in corrosion-resistant or corrosion-prone reaction vessels or autoclaves.

The reaction can preferably be effected in corrosion-resistant reaction vessels or autoclaves, for example made of glass, Teflon, enameled or coated steel, Hastelloy or tantalum.

The crude product suspension can be worked up as described in DE 10 2005 052 233.5.

The reaction to prepare organosilanes of the general formula I can be carried out in an open or a closed vessel and optionally under protective gas.

The reaction to prepare organosilanes of the general formula I can preferably be carried out under elevated pressure (>0.5 bar gauge). The elevated pressure may be between 20 and 0.5 bar, preferably 15 and 0.5 bar, more preferably from 10 to 0.5 bar, most preferably from 5 to 0.5 bar, gauge.

The reaction to prepare organosilanes of the general formula I can preferably be carried out with exclusion of air.

The further secondary constituents of hydrous alkali metal hydrogensulfides may be inert or reactive toward the starting materials used and/or the products formed in the preparation of compounds of the general formula I.

The crude product yield of the process according to the invention may be greater than 90%, preferably greater than 92%, more preferably greater than 95%, most preferably greater than 97%, based on the theoretical yield based on the amount of (haloorganyl)alkoxysilane used.

The crude product yield may be the gravimetrically determined sum of all isolated liquid compounds after solvents and solids have been removed.

The sulfur can be added in the form of sulfur powder, sulfur granule or in liquid form.

The process according to the invention has the advantage that merely the inventive reduction of alkali metal hydroxides in the sulfurizing reagents allows homogeneous monomer contents and hence reliable product qualities to be obtained.

The process according to the invention has the advantage that readily meterable, commercially available solids, for example hydrous sodium hydrogensulfide or sodium sulfide, are used as sulfurizing reagents.

The process according to the invention additionally has the advantage that it is possible to use commercially available, customary, hydrous sulfurizing raw materials. These hydrous, not specially prepared raw materials are advantageous compared to the alkali metal hydrogensulfides which are dried in a complicated manner (for example dried to <3% by weight).

A further advantage of the process according to the invention over known processes is the high conversions coupled with short batch times and temperatures which are simple to implement in technical terms.

A further advantage of the process according to the invention is the high crude product yields of liquid products which have not condensed to polysiloxanes. The process according to the invention exhibits high crude yields of liquid products.

A further advantage of the process according to the invention is the high monomer contents of the products which are detectable by $^{29}$Si NMR analysis.

A further advantage of the process according to the invention is that the solvent used contains more than 7.5% by weight of water and hence recycling of the solvent used is possible in a simpler and more attractive manner in technical and economic terms. From a technical point of view, less complicated separating operations and apparatus is needed for a separation of solvent and water. For example, in a distillative separation of solvent and water, less complicated columns and less energy expenditure are needed.

EXAMPLES

In the preparation of organosilanes, as specified in the examples and comparative examples, NaOH-free or NaOH-containing Na$_2$S from Tessenderlo or ICS Wolfen with from 30 to 40% by weight of water is used.

Analysis:

GC analysis for substances of the formula

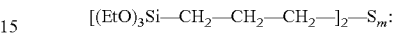
$[(EtO)_3Si-CH_2-CH_2-CH_2-]_2-S_m$:

The gas chromatography studies are carried out as described in ASTM method "Standard Test Method for Silanes Used in Rubber Formulations (Bis-(triethoxysilylpropyl)sulfanes): Characterization by Gas Chromatography (GC), D 6843-02".

The amounts of $(EtO)_3Si-CH_2-CH_2-CH_2-Cl$, $(EtO)_3Si-CH_2-CH_2-CH_2-SH$ and $[(EtO)_3Si-CH_2-CH_2-CH_2-]_2S$ present in the substance mixtures are obtained by GC (with internal standard).

HPLC analysis for substances of the formula

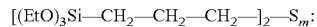
$[(EtO)_3Si-CH_2-CH_2-CH_2-]_2-S_m$:

The HPLC studies are carried out as described in ASTM method "Standard Test Method for Silanes Used in Rubber Formulations (Bis-(triethoxysilylpropyl)sulfanes): Characterization by High Performance Liquid Chromatography (HPLC), D 6844-02".

If mixtures of the organosilanes of the formula I contain compounds with $S_1$, the mean sulfur chain length is corrected taking account of the molecular weights and chain distribution determined.

$^1$H-NMR:

The $^1$H spectra are recorded on a Bruker Avance 500 NMR spectrometer with an analysis frequency for H of 500.13 MHz. The spectra are referenced internally against tetramethylsilane (TMS=0 ppm).

$^{29}$Si NMR:

The Si spectra are recorded on a Bruker Avance 500 NMR spectrometer with an analysis frequency for Si of 99.35 MHz (H NMR 500.13 MHz). The spectra are referenced internally against tetramethylsilane (TMS=0 ppm).

| Si-29 NMR data: | |
| --- | --- |
| ppm | Assignment |
| −45 to −47 | R-Si(OR')3 |
| −53 to −55 | R-Si(OR')2-O-Si |
| −62 to −66 | Si-O-Si(R)(OR')-O-Si |

The corrected integrals in the $^{29}$Si NMR are directly proportional to the proportions by weight of the monomers, dimers and trimers in the sample, it being assumed for the trimers that they are cyclic trimers with an (—O-(EtO)Si—O—)$_3$ structure.

Determination method of Na$_2$S, NaOH and NaSH in mixtures of sulfurizing reagents (feedstocks):

Solution A 100 g of sample are weighed accurately to 0.1 g into a 500 ml standard flask and dissolved with 200 ml of ultrapure water (CO$_2$-free). After the dissolution of the sample, the magnetic stirrer bar is removed, and the standard flask is made up to the mark with ultrapure water and shaken.

Solution B

A volumetric pipette is used to pipette an aliquot of 100 ml of the solution A to be analyzed into a further 500 ml standard flask. A measuring cylinder is used to add 50 ml of glycerol, ultrapure water is used to make up to the mark and the flask is shaken well.

Procedure of the Test

With the aid of a Dosimat, 80 ml of iodine solution and 25 ml of HCl solution are metered into a 250 ml Erlenmeyer flask. 10 ml of sample solution are taken from solution B with a pipette and added with gentle stirring (the pipette tip should be immersed into the solution). Rinse the walls of the flask with ultrapure water and, after adding approx. 5 ml of starch solution, titrate with thiosulfate solution until the color change from violet to colorless (very slowly just before the endpoint is reached).

Subsequently, add a few drops of phenolphthalein to the same solution (colorless but opaque) and titrate with NaOH solution until the color change from colorless to violet.

If less than 25 ml of NaOH solution is consumed, free NaOH is present in the sample (calculation 2); when the consumption is greater than 25 ml, the sample contains sodium hydrogensulfide (calculation 3).

The proportion by mass w of the $Na_2S$ in the technical grade $Na_2S$ is calculated by:

$$Na_2S \text{ content [\% by wt.]} = \{(V_I \times F_I) - (V_T \times F_T)\} \times 0.39 \times A$$

where:
$V_I$ 80 ml $c(I_2) = 0.05$ mol/l
$F_I$ titer of the iodide solution
$V_T$ consumption of $c(Na_2S_2O_3) = 0.1$ mol/l
$F_T$ titer of the thiosulfate solution
A dilution factor=2.5

The proportion by mass w of the NaOH in the technical grade $Na_2S$ is calculated by:
(when $Na_2OH<HCl$)

$$NaOH \text{ content [\% by wt.]} = \{(V_S \times F_S) - (V_{Na} \times F_{Na})\} \times 0.3999 \times A$$

$V_S$ 25 ml c(HCl)=0.1 mol/l
$F_S$ titer of the hydrochloric acid solution
$V_{Na}$ consumption of c(NaOH)=0.1 mol/l
$F_{Na}$ titer of the sodium hydroxide solution
A dilution factor=2.5

The proportion by mass w of the NaHS in the technical grade $Na_2S$ is calculated by:
(when NaOH>HCl)

$$NaHS \text{ content [\% by wt.]} = \{(V_{Na} \times F_{Na}) - (V_S \times F_S)\} \times 0.56 \times A$$

$V_{Na}$ consumption of c(NaOH)=0.1 mol/l
$F_{Na}$ factor of the sodium hydroxide solution
$V_S$ 25 ml c(HCl)=0.1 mol/l
$F_S$ factor of the hydrochloric acid solution
A dilution factor=2.5

Comparative Example 1

An unpressurized, nitrogen-blanketed reactor with an attached alkaline scrubber is initially charged with 140.0 kg of hydrous ethanol (contains 20.0% by weight of $H_2O$), 24 kg of $NaHCO_3$ (from Solvay, alkali metal hydroxide-free), 80.4 kg of $Na_2S$ hydrate (from ICS Wolfen, 60% with 0.9% by weight of NaOH and 0% by weight of NaSH) and 56.8 kg of ground sulfur (from Solvay, 200 mesh; alkali metal hydroxide-free) and mixed thoroughly with a stirrer. The alkali metal hydroxide content of the feedstocks is 0.44% by weight (calculation: 0.72 kg of NaOH/(24 kg+80.4 kg+56.8 kg)=0.72 kg/161.2 kg=0.44% by weight). The reactor contents are heated to 50° C. for 60 min. 312 kg of 3-chloropropyl(triethoxysilane) are metered into the reaction mixture in two portions 30 min apart. Within 180 min, colorless particles form in the reaction solution, and the viscosity of the suspension rises simultaneously. The suspension is separated using a centrifuge into solid and liquid constituents. The solvent is removed from the liquid phase by distillation under reduced pressure. An NMR analysis of the remaining liquid product shows, as silicon-containing constituents, predominantly hydrolyzed triethoxysilane species. The hydrolyzed triethoxysilane species are present predominantly in the form of oligomeric and polymeric siloxanes. The monomer content of the resulting products is, based on the amount of 3-chloropropyl(triethoxysilane) used, <10% by weight. The yield of the resulting products is, based on the amount of 3-chloropropyl(triethoxysilane) used, <10% by weight.

Comparative Example 2

An unpressurized, nitrogen-blanketed reactor with an attached alkaline scrubber is initially charged with 140.0 kg of hydrous ethanol (contains 20.0% by weight of $H_2O$), 24 kg of $NaHCO_3$ (from Solvay, alkali metal hydroxide-free), 40.2 kg of $Na_2S$ hydrate (from ICS Wolfen, 60% with 0.9% by weight of NaOH and 0% by weight of NaSH) and 56.8 kg of ground sulfur (from Solvay, 200 mesh; alkali metal hydroxide-free) and mixed thoroughly with a stirrer. The reactor contents are heated to 50° C. for 60 min. 312 kg of 3-chloropropyl(triethoxysilane) are metered into the reaction mixtures. Once the temperature has fallen to 54° C., two portions of 20.1 kg each of $Na_2S$ hydrate (from ICS Wolfen, 60% with 0.9% by weight of NaOH and 0% by weight of NaSH) are added to the suspension 30 min apart. The alkali metal hydroxide content of the feedstocks is thus 0.44% by weight (calculation: 0.72 kg of NaOH/(24 kg+80.4 kg+56.8 kg)=0.72 kg/161, 2 kg=0.44% by weight). The reaction solution comprising the feedstocks is heated to 55-60° C. for 120 min. The resulting suspension is cooled to 25-30° C. and separated using a centrifuge into solid and liquid constituents. The solvent is removed from the liquid phase by distillation under reduced pressure. 315 kg of liquid product are isolated. According to GC analysis, the product contains 6% by weight of 3-chloropropyl(triethoxysilane). The chain length m determined by HPLC is 3.78. A $^{29}Si$ NMR analysis of the product shows a monomer content of 81% by weight. The yield of the resulting product is 91%.

Example 1

An unpressurized, nitrogen-blanketed reactor with an attached alkaline scrubber is initially charged with 140.0 kg of hydrous ethanol (contains 20.0% by weight of $H_2O$), 24 kg of $NaHCO_3$ (from Solvay, alkali metal hydroxide-free), 20.1 kg of $Na_2S$ hydrate (from ICS Wolfen, 60% with 0.9% by weight of NaOH and 0% by weight of NaSH), 20.1 kg of $Na_2S$ hydrate (from ICS Wolfen, 62% with 0% by weight of NaOH and 1.35% by weight of NaSH) and 56.8 kg of ground sulfur (from Solvay, 200 mesh; alkali metal hydroxide-free) and mixed thoroughly with a stirrer. The reactor contents are heated to 50° C. for 60 min. 310 kg of 3-chloropropyl(triethoxysilane) are metered into the reaction mixture and the reaction solution is stabilized within the temperature range of 50-60° C. After 30 min, 10.05 kg of $Na_2S$ hydrate (from ICS Wolfen, 60% with 0.9% by weight of NaOH and 0% by weight of NaSH) and 10.05 kg of Na$_2$S hydrate (from ICS Wolfen, 62% with 0% by weight of NaOH and 1.35% by weight of NaSH) are metered into the suspension. After a further 30 min, another 10.05 kg of Na$_2$S hydrate (from ICS Wolfen, 60% with 0.9% by weight of NaOH and 0% by weight of NaSH) and 10.05 kg of Na$_2$S hydrate (from ICS Wolfen, 62% with 0% by weight of NaOH and 1.35% by weight of NaSH) are metered into the suspension. The alkali metal hydroxide content of the feedstocks is thus 0.22% by weight (calculation: 0.36 kg of NaOH/(24 kg+80.4 kg+56.8 kg)=0.36 kg/161.2 kg=0.22% by weight). The reaction solution comprising the feedstocks is heated to 55-65° C. for 120 min. The resulting suspension is cooled to 25-30° C. and separated using a centrifuge into solid and liquid constituents. The solvent is removed from the liquid phase by distillation under reduced pressure. 319 kg of liquid product are isolated. According to GC analysis, the product contains 3.1% by weight of 3-chloropropyl(triethoxysilane). The chain length m determined by HPLC is 3.78. A $^{29}$Si NMR analysis of the product shows a monomer content of 93.5% by weight. The yield of the resulting product is 93%.

Example 2

An unpressurized, nitrogen-blanketed reactor with an attached alkaline scrubber is initially charged with 140.0 kg of hydrous ethanol (contains 20.0% by weight of H$_2$O), 24 kg of NaHCO$_3$ (from Solvay, alkali metal hydroxide-free), 20.1 kg of Na$_2$S hydrate (from FMC Foret SA, 61% with 0% by weight of NaOH and 1.2% by weight of NaSH) and 56.8 kg of granular sulfur (from Rotoform, alkali metal hydroxide-free) and mixed thoroughly with a stirrer. The reactor contents are heated to 50° C. for 30 min. 303 kg of 3-chloropropyl(triethoxysilane) are metered into the reaction mixture and the reaction solution is stabilized within the temperature range of 50-60° C. After 30 min in each case, three portions each of 20.1 kg of Na$_2$S hydrate (from FMC Foret SA, 61% with 0% by weight of NaOH and 1.2% by weight of NaSH) are metered into the suspension. After the last Na$_2$S addition, 50 g of NaOH (from Aldrich) are metered into the reaction mixture. The alkali metal hydroxide content of the feedstocks is thus 0.03% by weight (calculation: 0.05 kg of NaOH/(24 kg+80.4 kg+56.8 kg)=0.05 kg/161.2 kg=0.03% by weight). The reaction solution comprising the feedstocks is heated to 55-65° C. for 120 min. The resulting suspension is cooled to 25-30° C. and separated using a centrifuge into solid and liquid constituents. The solvent is removed from the liquid phase by distillation. 323 kg of liquid product are isolated. According to GC analysis, the product contains 2.0% by weight of 3-chloropropyl(triethoxysilane). The chain length m determined by HPLC is 3.73. A $^{29}$Si NMR analysis of the product shows a monomer content of 97% by weight. The yield of the resulting product is 96.6%.

Example 3

137.0 kg of hydrous ethanol (contains 10.0% by weight of H$_2$O), 18 kg of NaHCO$_3$ (from Merck, alkali metal hydroxide-free), 56.8 kg of granular sulfur (from RAG Additive GmbH, alkali metal hydroxide-free) and 300 kg of 3-chloropropyl(triethoxysilane) are metered into an unpressurized, nitrogen-blanketed reactor with an attached alkaline scrubber, and the suspension is heated to 48-52° C. for 20 min. Subsequently, at intervals of 30 min in each case, five times 16.1 kg of Na$_2$S hydrate (from Tessenderlo, 60% with 0% by weight of NaOH and 1.0% by weight of NaSH) are metered into the suspension. After the fourth Na$_2$S addition, 20 g of NaOH (from Aldrich) are metered into the reaction mixture. The alkali metal hydroxide content of the feedstocks is thus 0.013% by weight (calculation: 0.02 kg of NaOH/(18 kg+80.5 kg+56.8 kg)=0.02 kg/155.3 kg=0.013% by weight). The reaction solution comprising the feedstocks is heated to 55-65° C. for 120 min. The solvent is removed from the resulting suspension by distillation under reduced pressure. The remaining suspension is separated with a centrifuge into solid and liquid constituents. 303.5 kg of liquid product are isolated. According to GC analysis, the product contains 1.7% by weight of 3-chloropropyl(triethoxysilane). The chain length m determined by HPLC is 3.76. A $^{29}$Si NMR analysis of the product shows a monomer content of 97.6% by weight. The yield of the resulting product is 92%.

Example 4

140.0 kg of hydrous ethanol (contains 15.0% by weight of H$_2$O), 18 kg of NaHCO$_3$ (from Merck, alkali metal hydroxide-free), 56.8 kg of granular sulfur (from RAG Additive GmbH, alkali metal hydroxide-free) and 300 kg of 3-chloropropyl(triethoxysilane) are metered into an unpressurized reactor with an attached alkaline scrubber, and the suspension is heated to 48-52° C. for 20 min. Subsequently, at intervals of 30 min in each case, five times 16.1 kg of Na$_2$S hydrate (from Tessenderlo, 60% with 0% by weight of NaOH and 1.0% by weight of NaSH) are metered into the suspension. The alkali metal hydroxide content of the feedstocks is thus 0.0% by weight. The reaction solution comprising the feedstocks is heated to 55-65° C. for 120 min. The solvent is removed from the resulting suspension by distillation under reduced pressure. The remaining suspension is separated with a centrifuge into solid and liquid constituents. 322 kg of liquid product are isolated. According to GC analysis, the product contains 1.3% by weight of 3-chloropropyl(triethoxysilane). The chain length m determined by HPLC is 3.76. A $^{29}$Si NMR analysis of the product shows a monomer content of 97.8% by weight. The yield of the resulting product is 97%.

Example 5

140.0 kg of hydrous ethanol (contains 20.0% by weight of H$_2$O), 24 kg of NaHCO$_3$ (from Merck, alkali metal hydroxide-free), 56.8 kg of granular sulfur (from RAG Additive GmbH, alkali metal hydroxide-free) and 309 kg of 3-chloropropyl(triethoxysilane) are metered into an unpressurized, nitrogen-blanketed reactor with an attached alkaline scrubber, and the suspension is heated to 48-52° C. for 20 min. Subsequently, at intervals of 30 min in each case, five times 16.1 kg of Na$_2$S hydrate (from Tessenderlo, 60% with 0% by weight of NaOH and 1.0% by weight of NaSH) are metered into the suspension. With each of the Na$_2$S additions, 20 g of NaOH are metered in in each case. The alkali metal hydroxide content of the feedstocks is thus 0.062% by weight (calculation: 0.1 kg of NaOH/(24 kg+80.5 kg+56.8 kg)=0.1 kg/161.3 kg=0.062% by weight). The reaction solution comprising the feedstocks is heated to 55-65° C. for 120 min. The resulting suspension is cooled to 25-30° C. and is separated using a centrifuge into solid and liquid constituents. The solvent is removed from the liquid phase by distillation under reduced pressure. 320 kg of liquid product are isolated. According to GC analysis, the product contains 3.5% by weight of 3-chloropropyl(triethoxysilane). The chain length m determined by HPLC is 3.76. A $^{29}$Si NMR analysis of the product shows a monomer content of 97.2% by weight. The yield of the resulting product is 94%.

Example 6

140.0 kg of hydrous ethanol (contains 20.0% by weight of $H_2O$), 24 kg of $NaHCO_3$ (from Merck, alkali metal hydroxide-free), 56.8 kg of granular sulfur (from CS Additive GmbH, alkali metal hydroxide-free) and 303 kg of 3-chloropropyl(triethoxysilane) are metered into an unpressurized, nitrogen-blanketed reactor with an attached alkaline scrubber, and the suspension is heated to 48-52° C. for 20 min. Subsequently, at intervals of 30 min in each case, five times 16.1 kg of $Na_2S$ hydrate (from Tessenderlo, 60% with 0% by weight of NaOH and 1.0% by weight of NaSH) are metered into the suspension. The alkali metal hydroxide content of the feedstocks is thus 0.0% by weight. The reaction solution comprising the feedstocks is heated to 55-65° C. for 120 min. The resulting suspension is separated with a centrifuge into solid and liquid constituents. The liquid constituents form an upper, reddish phase with a high water content and a lower, yellowish silane-containing phase. The two phases are separated and the silane-containing phase is freed of the solvent by distillation under reduced pressure. 306 kg of liquid product are isolated. According to GC analysis, the product contains 3.2% by weight of 3-chloropropyl(triethoxysilane). The chain length m determined by HPLC is 3.79. A $^{29}Si$ NMR analysis of the product shows a monomer content of 95.1% by weight. The yield of the resulting product is 92%.

The invention claimed is:

1. A process for preparing an organosilane of general formula I:

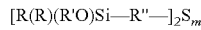

wherein:
R is the same or different and is a $C_1$-$C_8$-alkyl, $C_1$-$C_8$-alkenyl, $C_1$-$C_8$-aryl, $C_1$-$C_8$-aralkyl group, or an OR' group,
R' is the same or different and is a $C_1$-$C_{22}$ branched or unbranched monovalent alkyl or alkenyl group, an aryl group, an aralkyl group, a hydrogen, an alkyl ether group O—$(CR^{III}_2)$—O-Alk or O—$(CR^{III}_2)_y$—O-Alk or an alkyl polyether group O—$(CR^{III}_2O)_y$-Alk or O—$(CR^{III}_2$—$CR^{III}_2$—O)$_y$-Alk, where y=2-20, $R^{III}$ is independently H or an alkyl group and Alk is a branched or unbranched, saturated or unsaturated, aliphatic, aromatic or mixed aliphatic/aromatic monovalent $C_1$-$C_{22}$ hydrocarbon group,
R" is a branched or unbranched, saturated or unsaturated, aliphatic, aromatic or mixed aliphatic/aromatic divalent $C_1$-$C_{30}$ hydrocarbon group which is optionally substituted by F, Cl, Br, I, HS, $NH_2$ or NHR',
m is a mean sulfur chain length of from 1.5 to 4.5,
said process comprising reacting a (haloorganyl)alkoxysilane of formula II:

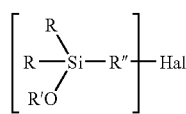

wherein R, R' and R"are each as defined above and Hal is chlorine, bromine, fluorine or iodine;
with a hydrous sulfurizing reagent comprising 15 to 60% by weight of water and alkali metal hydrogensulfide, metal sulfide $Me_2S$, metal polysulfide $Me_2S_g$ or any desired combinations thereof, where Me=alkali metal, $NH_4$ or (alkaline earth metal)$_{1/2}$, and g=1.5-8.0, and, optionally, additionally with sulfur and/or with $H_2S$ in a solvent consisting of an alcohol selected from the group consisting of methanol, ethanol, and propanol and, optionally, water,
wherein the alkali metal hydroxide content of all feedstocks is less than 0.44% by weight and wherein said process results in a product with greater than a 90% yield and a monomer content of greater than 90%.

2. The process of claim 1, wherein at least one additive is added before, during, or after the reaction.

3. The process of claim 2, wherein said said additive is a nonalcoholic solvent, or a polar, protic, aprotic, basic or acidic additive.

4. The process of claim 2, wherein said additive is $NaHCO_3$.

5. The process of claim 1, wherein said sulfurizing reagent includes $Me_2S$ and sulfur.

6. The process of claim 1, wherein said sulfurizing reagent is selected from the group consisting of: an alkali metal hydrogensulfide, $Me_2S$, $Me_2S_g$ and any desired combinations thereof.

7. The process of claim 1, wherein the reaction is carried out with exclusion of air.

8. The process of claim 1, wherein said solvent is menthanol.

9. The process of claim 1, wherein the alkali metal hydroxide content of all feedstocks is 0.0001-0.44% by weight.

10. The process of claim 1, wherein the alkali metal hydroxide content of all feedstocks is 0.0001-0.25 by weight.

11. The process of claim 1, wherein the alkali metal hydroxide content of all feedstocks is 0.001-0.015% by weight.

12. The process of claim 1, wherein said organosilane of formula I is selected from the group consisting of:
$[(MeO)_3Si(CH_2)_3]_2S$, $[(MeO)_3Si(CH_2)_3]_2S_2$, $[(MeO)_3Si(CH_2)_3]_2S_3$, $[(MeO)_3Si(CH_2)_3]_2S_4$, $[(MeO)_3Si(CH_2)_3]_2S_5$, $[(MeO)_3Si(CH_2)_3]_2S_6$, $[(MeO)_3Si(CH_2)_3]_2S_7$, $[(MeO)_3Si(CH_2)_3]_2S_8$, $[(MeO)_3Si(CH_2)_3]_2S_9$, $[(MeO)_3Si(CH_2)_3]_2S_{10}$.

13. The process of claim 1, wherein said organosilane of formula I is selected from the group consisting of:
$[(EtO)_3Si(CH_2)_3]_2S$, $[(EtO)_3Si(CH_2)_3]_2S_2$, $[(EtO)_3Si(CH_2)_3]_2S_3$, $[(EtO)_3Si(CH_2)_3]_2S_4$, $[(EtO)_3Si(CH_2)_3]_2S_5$, $[(EtO)_3Si(CH_2)_3]_2S_6$, $[(EtO)_3Si(CH_2)_3]_2S_7$, $[(EtO)_3Si(CH_2)_3]_2S_8$, $[(EtO)_3Si(CH_2)_3]_2S_9$, $[(EtO)_3Si(CH_2)_3]_2S_{10}$.

14. The process of claim 1, wherein said organosilane of formula I is selected from the group consisting of:
$[(C_3H_7O)_3Si(CH_2)_3]_2S$, $[(C_3H_7O)_3Si(CH_2)_3]_2S_2$, $[(C_3H_7O)_3Si(CH_2)_3]_2S_3$, $[(C_3H_7O)_3Si(CH_2)_3]_2S_4$, $[(C_3H_7O)_3Si(CH_2)_3]_2S_5$, $[(C_3H_7O)_3Si(CH_2)_3]_2S_6$, $[(C_3H_7O)_3Si(CH_2)_3]_2S_7$, $[(C_3H_7O)_3Si(CH_2)_3]_2S_8$, $[(C_3H_7O)_3Si(CH_2)_3]_2S_9$ and $[(C_3H_7O)_3Si(CH_2)_3]_2S_{10}$.

15. The process of claim 1, wherein said (haloorganyl)alkoxysilane of formula II is selected from the group consisting of:
3-chlorobutyl(triethoxysilane), 3-chlorobutyl(trimethoxysilane), 3-chlorobutyl(diethoxymethoxysilane), 3-chloroisobutyl(triethoxysilane), 3-chloroisobutyl(trimethoxysilane), 3-chloroisobutyl(diethoxymethoxysilane), 3-chloropropyl(triethoxysilane), 3-chloropropyl(trimethoxysilane), 3-chloropropyl(diethoxymethoxysilane), 2-chloroethyl(triethoxysilane), 2-chloroethyl(trimethoxysilane), 2-chloroethyl(diethoxymethoxysilane), 1-chloromethyl(triethoxysilane), 1-chloromethyl(trimethoxysilane), 1-chloromethyldiethoxymethoxysilane), 3-chlorobutyl (diethoxymethylsilane), 3-chlorobutyl(dimethoxymethylsilane), 3-chloroisobutyl(dimethoxymethylsilane), 3-chloroisobutyl(diethoxymethylsilane), 3-chloropropyl(diethoxymethylsilane), 3-chloropropyl (dimethoxymethylsilane), 2-chloroethyl(diethoxymethylsilane), 2-chloroethyl(dimethoxymethylsilane), 1-chloromethyl(diethoxymethylsilane), 1-chloromethyl (dimethoxymethylsilane), 3-chlorobutyl(ethoxydimethylsilane), 3-chlorobutyl(methoxydimethylsilane), 3-chloroisobutyl(methoxydimethylsilane), 3-chloroisobutyl(ethoxydimethylsilane), 3-chloropropyl (ethoxydimethylsilane), 3-chloropropyl(methoxydimethylsilane), 2-chloroethyl(ethoxydimethylsilane), 2-chloroethyl(methoxydimethylsilane), 1-chloromethyl (ethoxydimethylsilane) and 1-chloromethyl(methoxydimethylsilane).

16. The process of claim 6, wherein said organosilane of formula I is seleted from the group consisting of:
$[(MeO)_3Si(CH_2)_3]_2S$, $[(MeO)_3Si(CH_2)_3]_2S_2$, $[(MeO)_3Si(CH_2)_3]_2S_3$, $[(MeO)_3Si(CH_2)_3]_2S_4$, $[(MeO)_3Si(CH_2)_3]_2S_5$, $[(MeO)_3Si(CH_2)_3]_2S_6$, $[(MeO)_3Si(CH_2)_3]_2S_7$, $[(MeO)_3Si(CH_2)_3]_2S_8$, $[(MeO)_3Si(CH_2)_3]_2S_9$, $[(MeO)_3Si(CH_2)_3]_2S_{10}$, $[(EtO)_3Si(CH_2)_3]_2S$, $[(EtO)_3Si(CH_2)_3]_2S_2$, $[(EtO)_3Si(CH_2)_3]_2S_3$, $[(EtO)_3Si(CH_2)_3]_2S_4$, $[(EtO)_3Si(CH_2)_3]_2S_5$, $[(EtO)_3Si(CH_2)_3]_2S_6$, $[(EtO)_3Si(CH_2)_3]_2S_7$, $[(EtO)_3Si(CH_2)_3]_2S_8$, $[(EtO)_3Si(CH_2)_3]_2S_9$, $[(EtO)_3Si(CH_2)_3]_2S_{10}$, $[(C3H_7O)_3Si(CH_2)_3]_2S$, $[(C_3H_7O)_3Si(CH_2)_3]_2S_2$, $[(C_3H_7O)_3Si(CH_2)_3]_2S_3$, $[(C_3H_7O)_3Si(CH_2)_3]_2S_4$, $[(C_3H_7O)_3Si(CH_2)_3]_2S_5$, $[(C_3H_7O)_3Si(CH_2)_3]_2S_6$, $[(C_3H_7O)_3Si(CH_2)_3]_2S_7$, $[(C_3H_7O)_3Si(CH_2)_3]_2S_8$, $[(C_3H_7O)_3Si(CH_2)_3]_2S_9$ and $[(C_3H_7O)_3Si(CH_2)_3]_2S_{10}$.

17. The process of claim 16, wherein the reaction is carried out with exclusion of air.

18. The process of claim 17, wherein said solvent is menthanol.

19. The process of claim 18, wherein the alkali metal hydroxide content of all feedstocks is 0.0001-0.44% by weight.

20. The process of claim 18, wherein the alkali metal hydroxide content of all feedstocks is 0.001-0.015% by weight.

* * * * *